United States Patent [19]

Seemuth

[11] 4,405,333

[45] Sep. 20, 1983

[54] DIESEL FUEL COMPOSITION

[75] Inventor: Paul D. Seemuth, Oak Park, Mich.

[73] Assignee: Ethyl Corporation, Richmond, Va.

[21] Appl. No.: 423,606

[22] Filed: Sep. 27, 1982

[51] Int. Cl.[3] .............................................. C10L 1/22
[52] U.S. Cl. ......................................... 44/53; 44/57; 44/63; 44/56; 549/419
[58] Field of Search ..................... 44/53, 56, 57, 63; 549/419

[56] References Cited

U.S. PATENT DOCUMENTS

| | | | |
|---|---|---|---|
| 2,321,311 | 6/1943 | Mottlau et al. | 44/63 |
| 2,387,323 | 10/1945 | Gaynor et al. | 44/57 |
| 2,599,338 | 6/1952 | Lifson et al. | 44/63 |
| 2,858,200 | 10/1958 | Broughten | 44/57 |
| 3,311,559 | 3/1967 | Mottus | 44/63 |
| 3,380,815 | 4/1968 | Herbst | 44/57 |
| 4,191,536 | 3/1980 | Niebylski | 44/63 |

*Primary Examiner*—Charles F. Warren
*Assistant Examiner*—Y. Harris-Smith
*Attorney, Agent, or Firm*—Donald L. Johnson; John F. Sieberth; Joseph D. Olenweller

[57] ABSTRACT

The cetane number of diesel fuel is increased by the addition of a tetrahydropyranol nitrate ester, e.g. tetrahydro-2H-pyran-3-ol nitrate.

7 Claims, No Drawings

DIESEL FUEL COMPOSITION

BACKGROUND

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°–750° F. Recently, because of dwindling petroleum reserves, alcohol and alcohol-hydrocarbon blends have been studied for use as diesel fuel.

One major factor in diesel fuel quality is cetane number. Cetane number is related to ignition delay after the fuel is injected into the combustion chamber. If ignition delays too long, the amount of fuel in the chamber increases and upon ignition results in a rough running engine and increased smoke. A short ignition delay results in smooth engine operation and decreases smoke. Commerical petroleum diesel fuels generally have cetane number of about 40–55. Alcohols have a much lower cetane value and require the addition of a cetane improver for successful engine operation.

Through the years, many types of additives have been used to raise the cetane number of diesel fuel. These include peroxides, nitrites, nitrates, nitrosocarbamates, and the like. Alkyl nitrates such as amyl nitrate, hexyl nitrate and mixed octyl nitrates have been used commercially with good results.

SUMMARY

According to the present invention, the cetane rating of diesel fuel, either hydrocarbon or alcohol, is increased by the addition of a small but effective amount of a tetrahydropyranol nitrate.

DESCRIPTION OF THE PREFERRED EMBODIMENTS

A preferred embodiment of the invention is liquid fuel adapted for use in a diesel engine, said fuel being selected from the group consisting of liquid hydrocarbons of the diesel boiling range, alcohols, and mixtures thereof, said fuel containing a cetane increasing amount of a tetrahydropyranol nitrate.

Representative examples of these additive include:
4-methyltetrahydro-2H-pyran-3-ol nitrate
4-ethyltetrahydro-2H-pyran-3-ol nitrate
tetrahydropyran-2-ol nitrate
3-ethyltetrahydro-3H-pyran-4-ol nitrate
3-dodecyltetrahydro-3H-pyran-4-ol nitrate
3-methyl-tetrahydropyran-2-ol nitrate
5-chlorotetrahydro-2H-pyran-3-ol nitrate
4-bromotetrahydro-2H-pyran-3-ol nitrate
4-methyl-5-chlorotetrahydro-2H-pyran-3-ol nitrate, and the like. A more preferred class of pyranol nitrates include compounds having the structure:

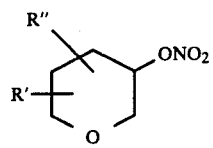

wherein R' and R" are independently selected from the group consisting of hydrogen, alkyl containing 1-20 carbon atoms, cycloalkyl containing 5-8 carbon atoms, alkenyl containing 2-20 carbon atoms, cycloalkyl containing 5-8 carbon atoms, alkenyl containing 2-20 carbon atoms, aryl containing 6-12 carbon atoms and aralkyl containing 7-12 carbon atoms. The remaining carbon bonds are hydrogen substituted.

Representative examples of this preferred embodiment include:
4,5-dimethyltetrahydro-2H-pyran-3-ol nitrate
4-octadecyltetrahydro-2H-pyran-3-ol nitrate
4-eicosyltetrahydro-2H-pyran-3-ol nitrate
4-allyltetrahydro-2H-pyran-3-ol nitrate
5- hexadecenyltetrahydro-2H-pyran-3-ol nitrate
4-eicosyltetrahydro-2H-pyran-3-ol nitrate
5-cyclopentyltetrahdyro-2H-pyran-3-ol nitrate
5-cyclohexyltetrahdyro-2H-pyran-3-ol nitrate
4-cyclooctyltetrahdyro-2H-pyran-3-ol nitrate
4-methyl-5-phenyltetrahydro-2H-pyran-3-ol nitrate
5-benzyltetrahydro-2H-pyran-3-ol nitrate
5-($\alpha,\alpha$-dimethylbenzyl)tetrahydro-2H-pyran-3-ol nitrate
5-(4-sec-pentylbenzyl)tetrahydro-2H-pyran-3-ol nitrate, and the like.

The most preferred cetane improver is tetrahydro-2H-pyran-3-ol nitrate.

The amount of cetane improver added depends on the type of fuel being used, the initial cetane value, and the amount of cetane number increase desired. Alcohol fuels such as methanol, ethanol, isopropanol, isobutanol, hexanol, and the like, have very low cetane values and large amounts of cetane improvers are required. A useful range in which to operate is about 5–25 weight percent cetane improver.

Blends of alcohol and petroleum derived diesel fuel have higher cetane values and require less cetane improver. A useful range is about 0.5–10 weight percent.

Petroleum derived distillate fuels in the diesel boiling range require only small amounts of cetane improver to achieve a significant increase in cetane number. Such fuels without any cetane improver generally have cetane numbers in the range of about 25–60. Cetane numbers in the range of 25–35 are considered low and those in the range of 50–60 are considered top grade diesel fuels. Diesel fuels in the 35–50 mid-range are most common. An object of the invention is to upgrade the low cetane number fuels at least into the mid-range and to increase the cetane value of the mid-range fuels into the upper portion of the mid-range (e.g. 45–50) or even into the premium range above 50. It has been found that highly beneficial results can be achieved using as little as 0.05 weight percent of the present additive. Accordingly, a useful concentration range in petroleum derived diesel fuel is about 0.01–5 weight percent and preferably about 0.05–0.5 weight percent.

The following example shows the preparation of a tetrahydropyranol nitrate by reaction of the corresponding hydroxy compound with mixed nitric acid-acetic anhydride.

EXAMPLE 1

In a reaction vessel was placed 50 ml acetic anhydride. While cooling, 14 ml of 90 percent fuming nitric acid was added. Following this, 25 g of tetrahydro-2H-pyran-3-ol was added dropwise at −8° to −10° C. over a one hour period. Stirring was continued for 1.5 hours at −10° C. The mixture was then allowed to warm to room temperature and then poured into an ice-water mixture. The organic phase settled and was separated.

The organic phase was diluted with methylene chloride and also washed with aqueous NaHCO$_3$ and dried over MgSO$_4$. The solvent was removed under vacuum leaving 24.04 g of tetrahydro-2H-pyran-3-ol nitrate. The structure was confirmed by IR and NMR analysis.

Other tetrahydropyranol nitrates can be made following the above general procedure by substituting other tetrahydropyranols.

The cetane increase caused by the present additives was measured in comparison with that caused by a commercial cetane improver, isooctyl nitrate, using a standard cetane engine. The fuel used was a blend of 46 cetane diesel fuel and 28 cetane light cycle oil giving a 38 cetane No. diesel fuel. The results at various concentrations of tetrahydro-2H-pyran-3-ol nitrate and isooctyl nitrate and isooctyl nitrate are shown in the following Table.

TABLE

| Concentration | Isooctyl Nitrate CN | Tetrahydro-2H—pyran-3-ol Nitrate CN |
|---|---|---|
| None | 38 | 38 |
| 0.15 | 41.64, 41.65 | 42.24, 42.38 |

Other conventional additives may be included in the diesel fuel including antioxidants, pour point depressants, cold filter plugging inhibitors, detergents, rust inhibitors, and the like including other cetane improvers.

I claim:

1. Liquid fuel adapted for use in a diesel engine, said fuel being selected from the group consisting of liquid hydrocarbons of the diesel boiling range, alcohols and mixtures thereof, said fuel containing a cetane number increasing amount of a tetrahydropyranol nitrate.

2. A fuel composition of claim 1 wherein said fuel is said liquid hydrocarbon of the diesel boiling range.

3. A fuel composition of claim 2 wherein said tetrahydropyranol nitrate has the structure

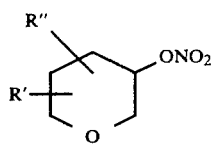

wherein R' and R are independently selected from the group consisting of hydrogen, alkyl containing 1–20 carbon atoms, cycloalkyl containing 5–8 carbon atoms, alkenyl containing 2–20 carbon atoms, aryl containing 6–12 carbon atoms and aralkyl containing 7–12 carbon atoms.

4. A fuel composition of claim 3 wherein said tetrahydropyranol nitrate is the compound tetrahydro-2H-pyran-3-ol nitrate.

5. A cetane number increasing tetrahydropyranol nitrate additive having the structure

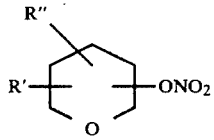

wherein R' and R" are independently selected from the group consisting of hydrogen, alkyl containing 1–20 carbon atoms, cycloalkyl containing 5–8 carbon atoms, alkenyl containing 2–20 carbon atoms, aryl containing 6–12 carbon atoms and aralkyl containing 7–12 carbon atoms.

6. An additive of claim 5 wherein the nitrate group is in the 3 position.

7. A additive of claim 6 wherein said additive is the compound tetrahydro-2H-pyran-3-ol nitrate.

* * * * *